(12) United States Patent
Dahlstrand

(10) Patent No.: US 8,690,795 B2
(45) Date of Patent: Apr. 8, 2014

(54) DEVICE FOR TESTING NEEDLES

(75) Inventor: Christer Dahlstrand, Göteborg (SE)

(73) Assignee: AB Christer Dahlstrand, Göteborg (SE)

( * ) Notice: Subject to any disclaimer, the term of this patent is extended or adjusted under 35 U.S.C. 154(b) by 157 days.

(21) Appl. No.: 13/056,656

(22) PCT Filed: Jul. 30, 2009

(86) PCT No.: PCT/SE2009/050914
§ 371 (c)(1),
(2), (4) Date: Jan. 29, 2011

(87) PCT Pub. No.: WO2010/014034
PCT Pub. Date: Feb. 4, 2010

(65) Prior Publication Data
US 2011/0130680 A1    Jun. 2, 2011

(30) Foreign Application Priority Data

Aug. 1, 2008  (SE) ...................................... 0801748

(51) Int. Cl.
*A61B 10/02*  (2006.01)
*A61B 19/00*  (2006.01)

(52) U.S. Cl.
CPC ........... *A61B 10/0233* (2013.01); *A61B 19/201* (2013.01); *A61B 2010/0225* (2013.01); *A61B 2019/5276* (2013.01)
USPC ........................................................ 600/567

(58) Field of Classification Search
USPC ................................................ 600/564, 567
See application file for complete search history.

(56) References Cited

U.S. PATENT DOCUMENTS

| | | | |
|---|---|---|---|
| 4,555,243 A | 11/1985 | Markham | |
| 4,695,273 A * | 9/1987 | Brown | 604/173 |
| 4,989,614 A * | 2/1991 | Dejter et al. | 600/565 |
| 5,060,658 A * | 10/1991 | Dejter et al. | 600/566 |
| 5,415,182 A * | 5/1995 | Chin et al. | 600/567 |
| 5,788,713 A * | 8/1998 | Dubach et al. | 606/130 |
| 6,009,347 A * | 12/1999 | Hofmann | 604/21 |
| 6,171,249 B1 * | 1/2001 | Chin et al. | 600/461 |

(Continued)

FOREIGN PATENT DOCUMENTS

SE    521675 C2    11/2003
WO    93/22971 A1    11/1993

OTHER PUBLICATIONS

Swedish Patent Office, Int'l Search Report in PCT/SE2009/050914, Oct. 23, 2009.

(Continued)

*Primary Examiner* — Jeffrey G Hoekstra
*Assistant Examiner* — Michael C Stout
(74) *Attorney, Agent, or Firm* — Piedmont Intellectual Property

(57) ABSTRACT

The present invention relates to a device (1) to allow providing testing of tissue of prostate gland (3) using two or more biopsy needles (4, 5, 6, etc.) essentially simultaneously. According to the invention a guiding (7) for said needles (4-6) is arranged to act on said needles, which preferably have a built-in curvature,-.so that the needles (4-6) are curved by said guiding to get the needles, when using the device, to extend along a peripheral part of the prostate gland (3) in question to allow testing in said peripheral part (2) of the same.

1 Claim, 4 Drawing Sheets

(56) References Cited

U.S. PATENT DOCUMENTS

Figure 5:
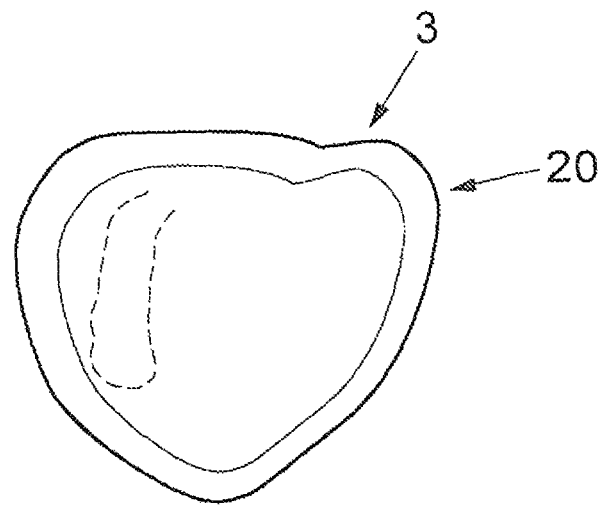

| | | | |
|---|---|---|---|
| 6,217,554 B1 * | 4/2001 | Green | 604/164.01 |
| 6,302,870 B1 * | 10/2001 | Jacobsen et al. | 604/272 |
| 6,325,796 B1 * | 12/2001 | Berube et al. | 606/33 |
| 6,419,641 B1 * | 7/2002 | Mark et al. | 600/564 |
| 6,592,559 B1 * | 7/2003 | Pakter et al. | 604/272 |
| 6,626,902 B1 * | 9/2003 | Kucharczyk et al. | 606/41 |
| 6,730,061 B1 * | 5/2004 | Cuschieri et al. | 604/158 |
| 7,833,168 B2 * | 11/2010 | Taylor et al. | 600/567 |
| 8,012,139 B2 * | 9/2011 | McKay et al. | 604/506 |
| 8,083,722 B2 * | 12/2011 | McKay | 604/173 |
| 2002/0151867 A1 * | 10/2002 | McGuckin et al. | 604/506 |
| 2005/0272975 A1 * | 12/2005 | McWeeney et al. | 600/113 |
| 2006/0259006 A1 * | 11/2006 | McKay et al. | 604/506 |
| 2010/0056900 A1 * | 3/2010 | Whitcomb et al. | 600/414 |
| 2011/0213300 A1 * | 9/2011 | McWeeney et al. | 604/95.04 |
| 2012/0108951 A1 * | 5/2012 | Van Der Lugt et al. | 600/411 |

OTHER PUBLICATIONS

Swedish Patent Office, Int'l Preliminary Report on Patentability in PCT/SE2009/050914, Feb. 10, 2011.

* cited by examiner

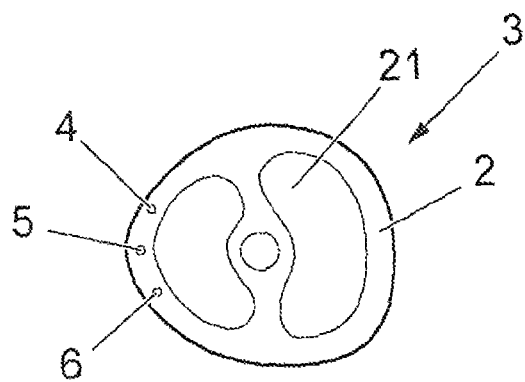
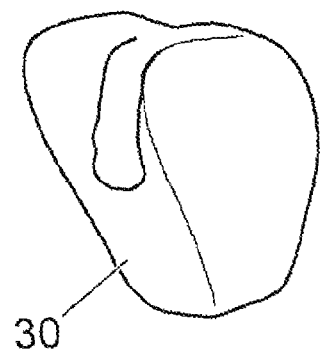
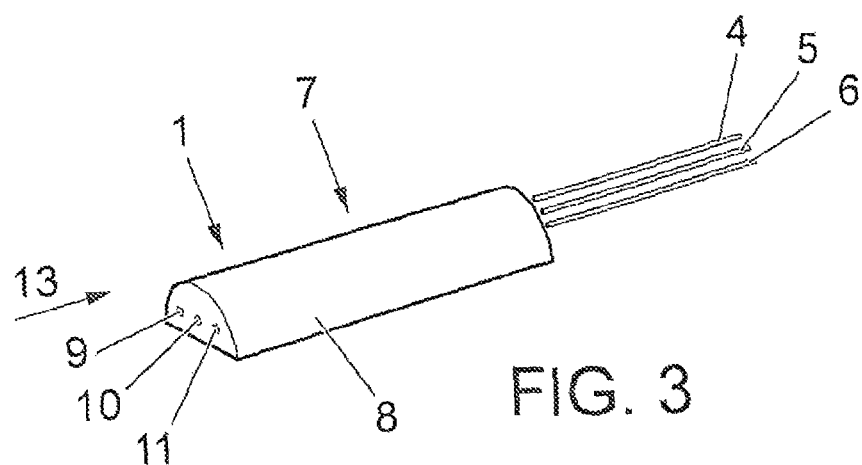
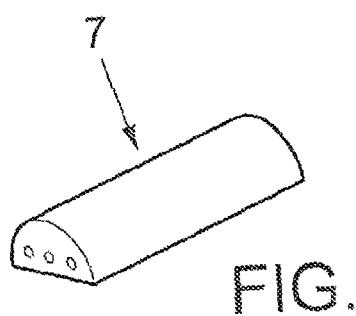

DEVICE FOR TESTING NEEDLES

The present invention relates to a device to allow providing testing of tissue of prostate gland using two or more biopsy needles essentially simultaneously.

According to known solutions to obtain a plurality of biopsies in a common testing stick, particularly the prostate gland, a plurality of needles are utilized simultaneously or at least essentially simultaneously.

Upon examination of tissue due to suspected disease, control of, or for another reason, a plurality of methods may be used, e.g., x-ray, ultrasound, blood testing and other techniques. It is usually occurring that a tissue specimen is desired, a so-called biopsy. This particularly applies when it may be a question of a malignant disease, i.e., cancer. Said test is usually taken by means of some form of needle, which is hollow so that a cylindrical core of tissue is obtained. The needle can be injected manually or by means of different instruments, e.g., spring-loaded so-called biopsy guns. Aiming is manual or effected by means of ultrasound, x-ray or other equipment. Usually, a plurality of biopsies are taken. For a plurality of reasons, it is not possible to take too many, foremost because each stick is painful for the patient. An organ that often is examined is the prostate, where it is common that six biopsies are taken. Unfortunately, then the part of the organ that actually has been examined is small. For instance, six biopsies of 1.2 mm in diameter and 20 mm long are usually taken from prostate. The proper gland maybe has a volume of approx. 50 $cm^3$, and it is therefore only a few percent of the gland from which specimens actually have been obtained. It is furthermore so that in many cases, changes less than a certain size are attached less importance. They are considered so small that they do not give rise to any action in the form of, e.g., operation, but can continue to be controlled.

By U.S. Pat. No. 5,415,182 A, a biopsy instrument provided with multi-needles is previously known, but wherein all needles are arranged in parallel and to move in different paths at mutual distance from each other laterally, as seen transversely to the length extension and direction of motion of the needles. There are problems also with instruments of the type mentioned above, since testing is carried out in a common direction with all needles and that the examined area accordingly becomes small and slender. In that connection, the instrument becomes also ungainly and cannot be directed by means of, e.g., ultrasound.

Also by SE 521 675 C2, a device is known for testing with a plurality of needles at the same time, and where some needle is guided in another path than the other needle/needles. However, there is no solution to provide a curved spherical path for the needles.

It is namely the area along the circumference of the prostate gland that is interesting and that it is desired to examine, i.e., under the surface of the proper prostate in a spherical layer area. Thus, it is desired to take a plurality of samples in said area simultaneously and without taking anything from the remaining part of the prostate.

THE OBJECT OF THE INVENTION

Therefore, the main object of a present invention is primarily to solve said problems by means of a device that performs the functions by simple and efficiently acting means.

THE MOST IMPORTANT FEATURES OF THE INVENTION

Said object is attained by means of a device according to the present invention that essentially is characterized in that a guiding for said needles is arranged to act on said needles, which preferably have built-in curvature, so that the needles are curved by said guiding to extend along a peripheral part of the prostate gland in question to allow testing in said spherical peripheral part.

LIST OF FIGURES

Figure 6:
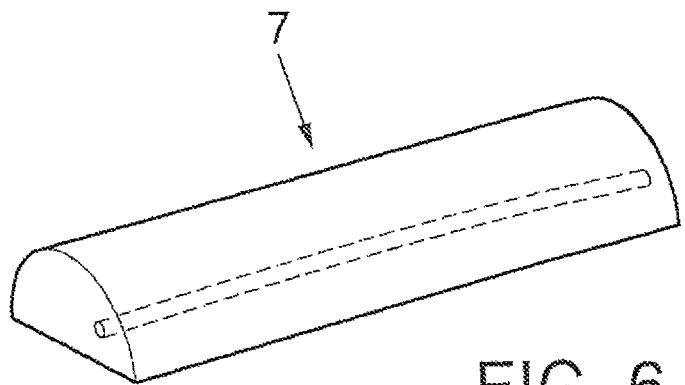
Figure 7:
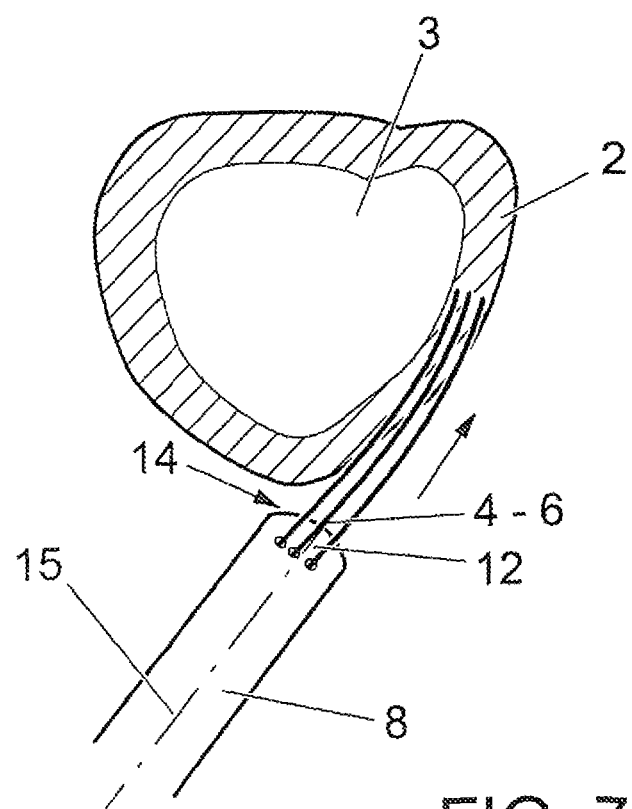
Figures 8, 9, 10:
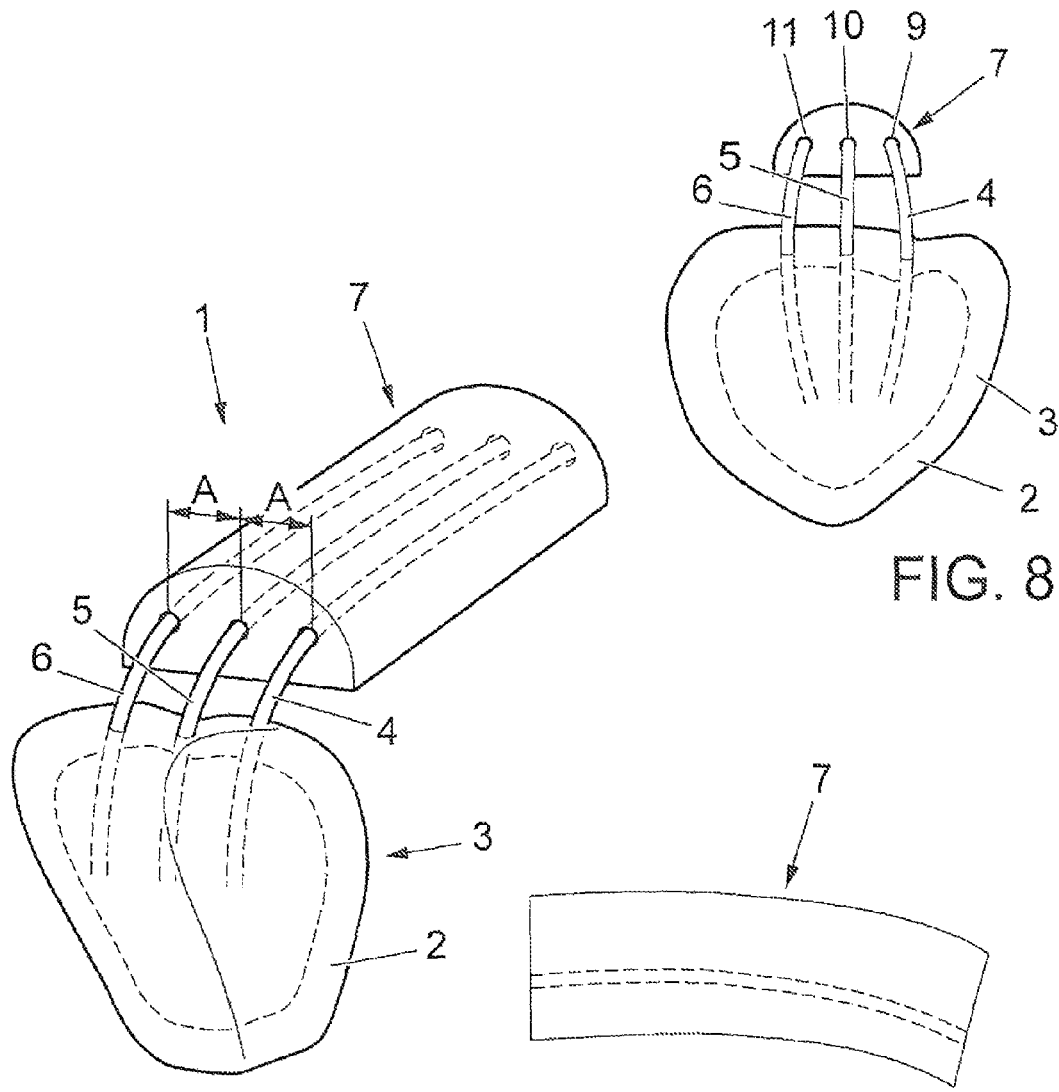

The invention is described below in the form of a number of preferred embodiment examples, reference being made to the accompanying drawings, in which, FIG. 1 schematically shows a prostate gland with the intended outer peripherally spherical area intended for testing, having marked needles, FIG. 2 shows in perspective the prostate, FIGS. 3-4 show a jig for the needles as seen from different sides, FIG. 5 shows the area intended for testing, FIG. 6 shows a jig having shown needle guiding, FIG. 7 shows a variant of needle guiding, FIGS. 8-9 show in more detail needle guiding, and FIG. 10 shows a prostate gland with needle-stick pattern in layers therein and the gland as seen from outside.

Testing using a plurality of needles simultaneously is disclosed and is clearly seen in said SE 521 675 C2.

On one hand, the invention is based on the fact that if a plurality of tissue specimens are taken simultaneously, more samples are obtained faster, there will be fewer sticks using double or triple sticks or more. The human body cannot distinguish if there is one or more sticks if they are close together, e.g., with spaces of 3 mm, and if the sticking is carried out simultaneously. That is, a double or triple stick does not hurt more than a single stick and, e.g., four triple sticks=twelve biopsies feel like four single sticks that only provide four biopsies.

Furthermore, a volume effect is gained when, e.g., three biopsies are taken in a fixed form, e.g., in a triangle. The part of a tissue on which it is possible to give an opinion whether there are tumours or changes of a certain size. The volume being possible give an opinion on in this way may increase tenfold or more. That is, if the needles, e.g., are placed at 3 mm distances in a triangle, a fixed volume is obtained where it for certain is possible to say that there are no changes that have a size of 3 mm.

In the drawings, it is shown how the invention may be applied upon testing of the prostate gland and in that connection a common holder is utilized for the needles and the sleeves, respectively. Said common holder is formed of a jig that has a central opening for attachment of the jig on a transmitter and receiver, not shown, which operates by means of ultrasound. In that connection, the needles are coupled, with the respective rear portions thereof, together with a control device, which in a known way is arranged to be inserted in a gun of, for instance, the type that is shown in the above-mentioned U.S. Pat. No. 5,415,182 A. At a first stage, the needles are first actuated to be displaced in the direction out of the appurtenant inner sleeve and that then the inner sleeves are displaced out in the direction so that the needles are surrounded by the same. All is carried out by means of spring-force actuation and happens so fast that it is perceived as a common needle-stick. After that, also the common withdrawal of needles and inner sleeves is carried out in the same moment. In that connection, a tissue specimen has been removed from the intended test site by means of the respective recess of the respective needle and surrounding cut-off inner tube. Needles and inner tubes have a tip each so that they easily penetrate into the test object and take desired tissue specimens.

The invention allows applying a testing technique for tissue testing wherein examined volume of tissue regarding changes of a certain size is desired by two or more needles being injected in a determined geometrical pattern, and wherein the pain decreases for the patient by the fact that a plurality of biopsy needles are injected simultaneously at such a distance from each other that the body perceives this as a single stick.

Two or more biopsy needles are guided in a determined geometrical pattern by a number of tubes or channels in which the biopsy needles are stuck simultaneously and thereby are guided in the tissue that is to be examined.

However, there is nothing mentioned therein about any guiding device of a plurality of needles in curved shape along the periphery of a sphere, but in other respects, it can be understood therefrom which technique that is utilized. Therefore, reference is made to said patent so as to avoid excessive repetition of the text therein.

A device 1 to allow providing testing of a tissue 2 of a prostate gland 3 using two or more biopsy needles 4, 5, 6, etc., essentially simultaneously in a common needle-stick procedure comprises, according to the present invention, a guiding 7 for said needles 4-6. The device 1 comprises separate guidings for each needle 4-6 individually or a common guiding for guiding of all needles simultaneously.

Said guiding 7 is arranged to act on said needles 4-6, which, on one hand, may have a built-in curvature from the beginning, so that the needles 4-6 are curved by said guiding 7 to extend along a peripheral part of the prostate gland 3 in question during the proper testing, to allow testing in said interesting peripheral part 2 of the prostate gland 3 and accordingly not in the intermediate part 21 thereof being not so interesting, in that connection, for measuring purposes. The needles 4-6 are hollow so that a core-shaped specimen is taken with each needle.

The guiding 7 is formed of a jig 8, which has separate guide grooves 9 10, 11, etc., fitting the needles 4-6 in question, or a common curved surface 12, along which said needles 4-6 are arranged to extend and be guided upon motion actuation in the axial direction 13 of the respective needles 4-6 in a common stage.

According to the invention, the guiding 7, 12 for said needles 4-6 is double-curved and the needles 4-6 are arranged to be received and guided at a mutually located maintained distance A from each other in a jig 8, having guide channels/guide grooves 9-11 therein, or by a common sphere-shaped part 14 against the double-curved surface 12 of which the needles 2-6 are arranged to be guided in the direction from the centre 15 of said part 14 for providing a spherical needle guiding.

A said jig 8 comprises attachment means so as to be attachable on an ultrasound probe or on another apparatus intended for transparent examination of the body.

There are three or more needles 4-6, at least one needle of which has a path of curvature different from other needles.

Said needles 4-6 are arranged in a curved way to assume a path of motion 30 each that extends along the outer limiting surface 20 of the spherical measurement body in question upon common pressing-in into said guiding/guidings 7, 12. The guiding/guidings 7, 12 is/are arranged to guide the needles 4-6 to extend at a common distance from the centre 21 of the sphere of the measurement object 3 in question. Preferably, there is a common spring-actuation of all needles 4-6 arranged to be provided in the direction of withdrawal of the needles 4-6.

With reference to FIG. 7, the needles 4-6 are, in that connection, shown during testing of a prostate 3 along a testing side of the same.

The spreading planes of the respective needles 4-6 are spread along the plane of the picture and with a needle approx. 5 mm above and with another needle approx. 5 mm below said plane of the picture, respectively.

The nature and function of the device according to the invention should have been understood from what has been said above and from what has been shown in the drawings but the invention is naturally not limited to the embodiments described above and shown in the accompanying drawings. Modifications are feasible, particularly as for the nature of the different parts, or by using an equivalent technology, without departing from the protection area of the invention, such as it is defined in the claims.

The invention claimed is:

1. A device for enabling testing of prostate gland tissue using two or more biopsy needles approximately simultaneously, comprising:
   a guide for the biopsy needles that is arranged to act on the needles such that the needles are curved by the guide to extend along a peripheral part of a prostate gland under test, enabling testing in a curved peripheral part of the prostate gland;
   wherein the guide comprises a jig having either separate guide grooves that fit the biopsy needles or a common curved surface, and the guide is arranged to guide the biopsy needles to extend a common distance from a center of a prostate gland under test;
   the biopsy needles are arranged to extend and be guided along the separate guide grooves or the common curved surface upon motion actuation of the needles;
   the guide is double-curved, and when the jig has separate guide grooves, the guide grooves are double-curved; and when the jig has the common curved surface, the guide has a spherically shaped part against which the biopsy needles are arranged to be guided in a direction from a center of the spherically shaped part;
   the biopsy needles are arranged to be received by the guide and guided at a mutually maintained distance from each other, and the biopsy needles are curved to move along respective paths that extend along an outer limiting surface of the peripheral part of the prostate gland upon pressing the needles into the guide;
   the jig is configured to be attachable to an apparatus for examining the prostate gland; and
   the guide is arranged to act on three or more biopsy needles, at least one of which has a curved path that is different from curved paths of other needles; and
   a spring configured for urging the biopsy needles in a direction of withdrawal of the needles.

* * * * *